United States Patent
Abraham et al.

(12)
(10) Patent No.: US 6,734,969 B2
(45) Date of Patent: May 11, 2004

(54) VACUUM MEASUREMENT DEVICE

(75) Inventors: Michael Abraham, Mainz (DE); Matthias Hampel, Rüsselsheim (DE)

(73) Assignee: Nanophotonics AG, Mainz (DE)

( * ) Notice: Subject to any disclaimer, the term of this patent is extended or adjusted under 35 U.S.C. 154(b) by 231 days.

(21) Appl. No.: 09/940,407

(22) Filed: Aug. 27, 2001

(65) Prior Publication Data

US 2002/0101591 A1 Aug. 1, 2002

(30) Foreign Application Priority Data

Aug. 28, 2000 (DE) .......................... 100 42 123

(51) Int. Cl.[7] .................................. G01J 4/00
(52) U.S. Cl. ...................................... 356/369
(58) Field of Search ........................ 356/369, 601, 356/630, 632; 355/77, 53

(56) References Cited

U.S. PATENT DOCUMENTS 4,115,736 A    9/1978  Tracy
4,829,178 A *  5/1989  Waugh .................. 250/309
5,046,849 A    9/1991  Severin et al.
5,519,491 A *  5/1996  Gaechter et al. ........ 356/486
5,764,365 A *  6/1998  Finarov .................. 356/630

FOREIGN PATENT DOCUMENTS

EP    0 119 679    9/1984
WO    91/16600     10/1991

* cited by examiner

Primary Examiner—David Gray
Assistant Examiner—D. Ben Esplin
(74) Attorney, Agent, or Firm—Hudak, Shunk & Farine Co. LPA

(57) ABSTRACT

To carry out measurements in the vacuum, for example for quality control in the production of semiconductors, conventional stand alone measuring machines are installed. They are very cost, space and time intensive. To enable a process oriented measurement under optimal conditions, a device with a two part case is proposed that can be moved in a vacuum chamber, whereby one part of the case projects into the vacuum chamber and the other part of the case is located outside the vacuum chamber. The case can receive a measurement system. In addition, an adjusting device, engaging with the case, and a counterpull device, engaging with the second part of the case, are provided.

18 Claims, 12 Drawing Sheets

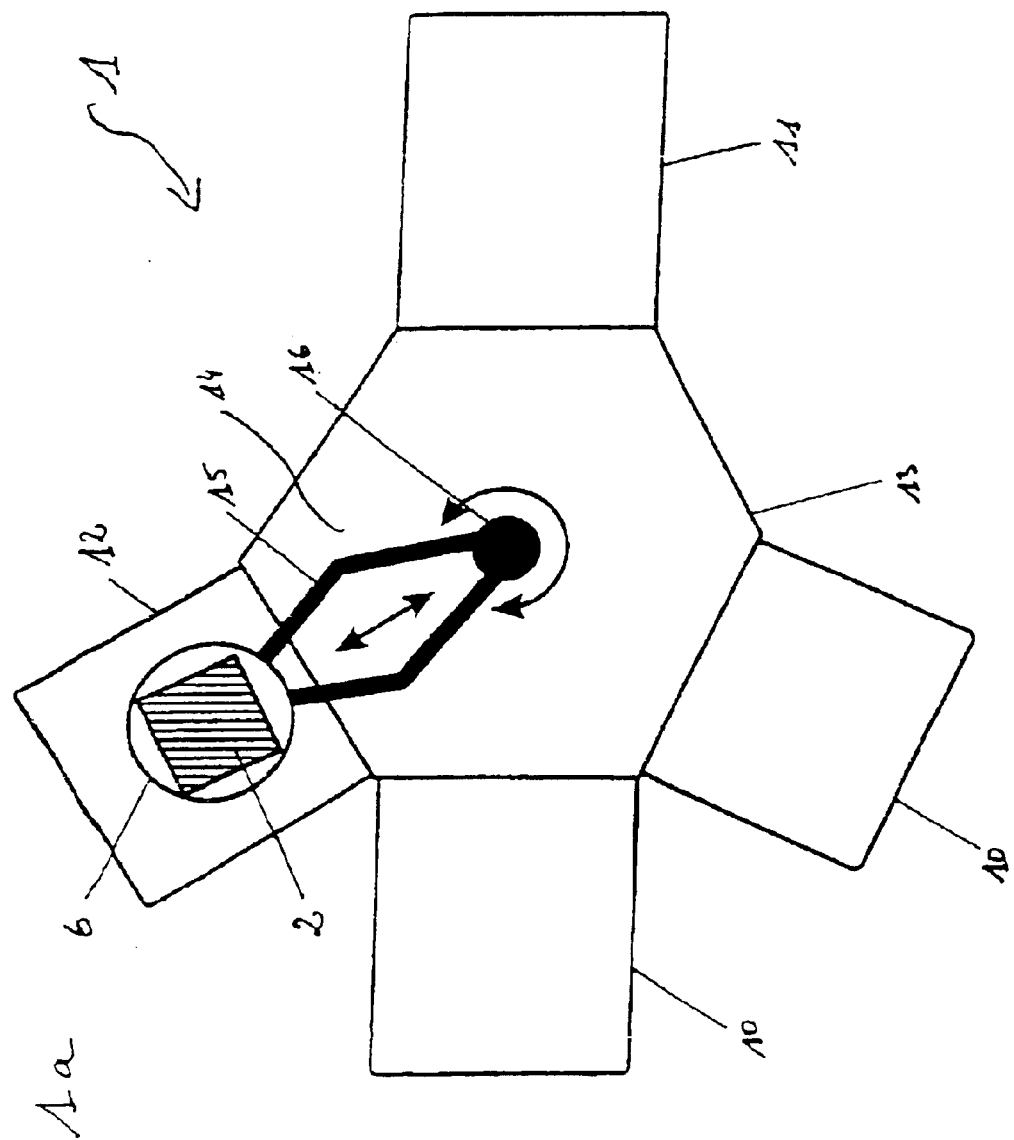

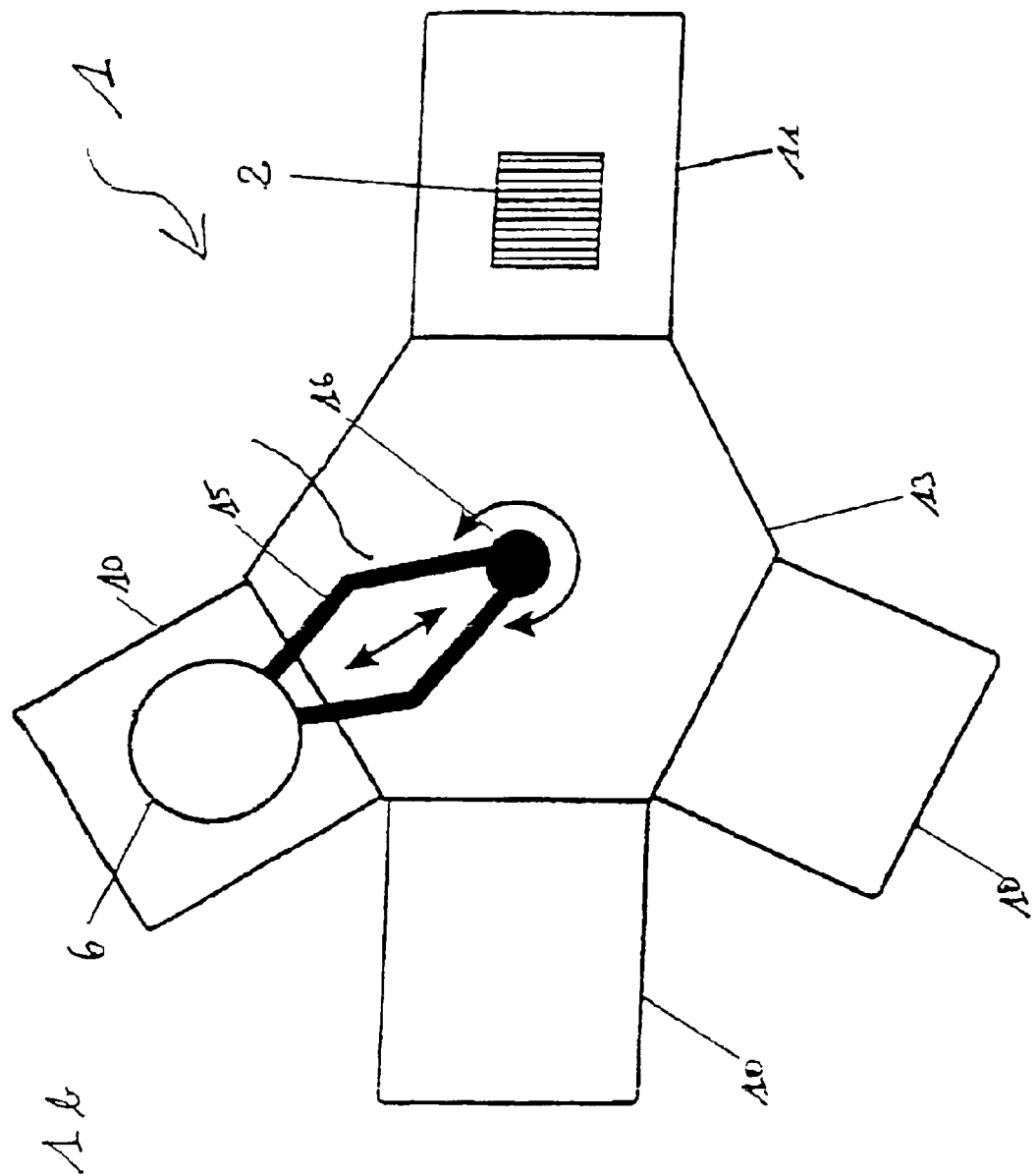

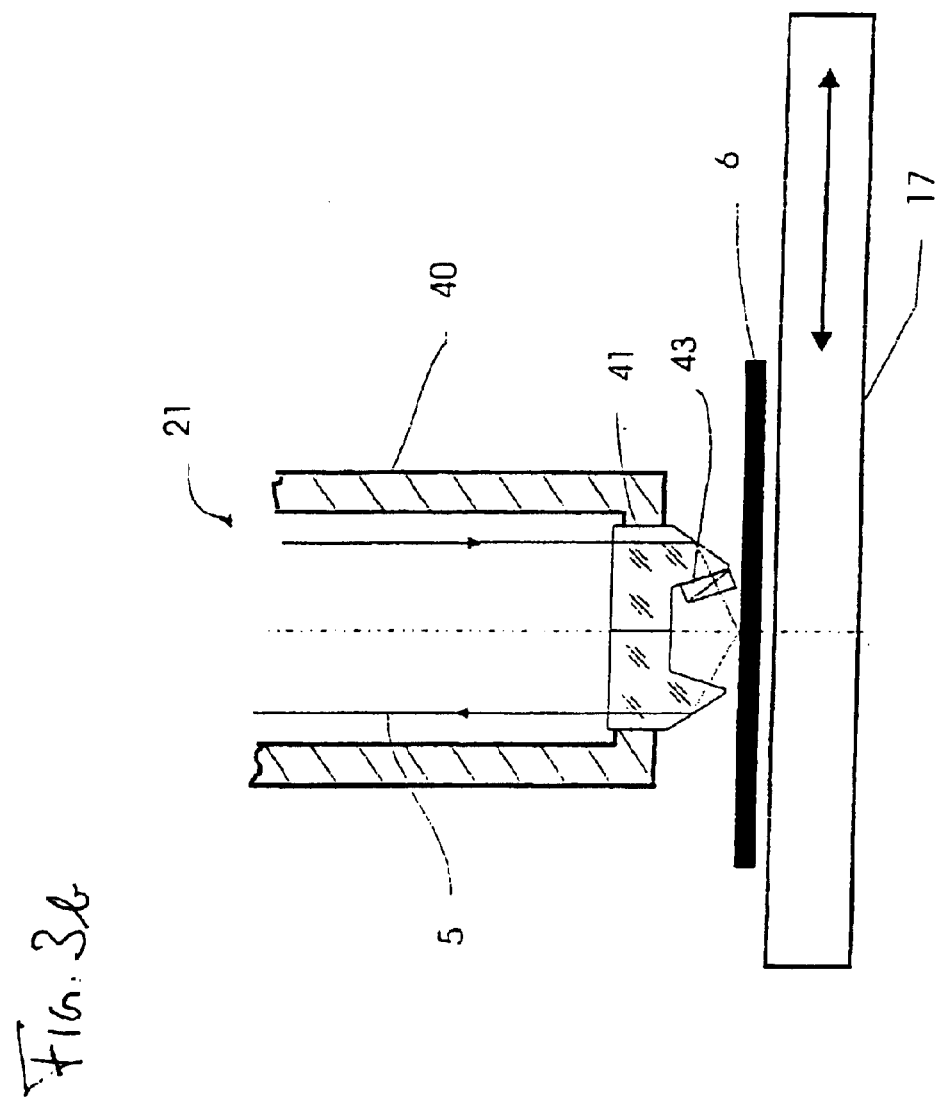

VACUUM MEASUREMENT DEVICE

FIELD OF THE INVENTION

The invention relates to a device to carry out measurements in a vacuum chamber, in particular to measure thin layers, with a case, exhibiting at least one measurement window, to receive a measurement system.

Furthermore, the invention relates to a vacuum adapter for mechanisms to carry out optical measurements in a vacuum chamber.

Measurements in the vacuum, in particular for quality control, are quite important, for example, in the production of semiconductors. The most frequent variables to be measured are, for example, the thickness of the thin functional layers ranging from a few nanometers to some micrometers and the size and distribution of the particles. With the transition to smaller structures and larger wafer diameters, the demand for process-accompanying quality control increases. The goal is the early detection of errors and the correction of process parameters to increase the yield and the productivity of the production process. The higher the requirements of the quality control are, the more often the wafers have to leave the production process in order to be subjected to a random measurement.

BACKGROUND OF THE INVENTION

The state of the art includes the so-called stand alone measuring machines, which are installed at central points of the plant. Due to the high cost of these systems and the relatively high space requirement, only a few of these systems can be installed. One drawback is also the additional paths, the additional loading and unloading steps of the wafers from the transport boxes and back again. Moreover, much time is lost between the detection of a defect and the reaction, a state that can result in enormous losses as the process speed increases and the value of the individual wafers increases dramatically.

To improve the yield and to reduce the production cycles precisely in thin film production, the layer properties of the thin films should be measured as process oriented as possible. One preferred method for measuring the refractive index and the thickness of thin layers is ellipsometry. It exploits the change in the polarization state of the light after its reflection on the sample surface. In addition, the collimated and fully polarized light is focused on the sample at a specific angle of incidence. In addition to the reflection, the polarization state of the radiation changes as a function of the properties of the sample.

In the case of ellipsometric measurements for determining the coating parameters in production processes not only stand alone machines have been used, but there has also been an attempt to measure the coating parameters in situ. The EP 0 527 150 B1 proposes an arrangement for ellipsometric in situ measurements in an industrial coating system. The ellipsometer, according to the EP 0 527 150 B1, exhibits a so-called paddle, on which not only the wafers to be measured are disposed but also the analyzing and the polarizing unit as well as the beam deflecting units are disposed in the form of prisms. Both for the incident beam and for the reflected beam a tube is provided as the beam tube. In a preferred embodiment these two tubes are also fastened to the paddle.

This ellipsometer arrangement has grave drawbacks. To carry out the measurement with an adequately good angle of incidence (usually between 65 and 75 degrees), it is a drawback with respect to production engineering that the coating furnace, which was optimized for a high throughput, cannot be fully filled, because minimum spacing must be maintained between the wafer to be measured and its neighboring wafer. Since the coating furnace is filled differently than what would correspond to the optimized state, the flow conditions in the furnace change and thus the quality of the coating.

From the view point of measurement technology it is quite disadvantageous that the pumps, which are typical in a vacuum chamber, excite the tube and the paddle to self sustained oscillation, the results of which are falsified measurements. The high temperatures and gases, generated during production, have a negative impact on the measurement results, since prism wall deposits and thermally induced stresses can be expected.

SUMMARY OF THE INVENTION

The object of the invention is to provide a device to carry out the measurements in the vacuum. Said device ought not to exhibit either the drawbacks of the stand alone devices or the in situ measuring devices, but rather permit a process oriented measurement under optimal measurement conditions.

This problem is solved by a device, according to claim 1. In addition, the problem is solved by a vacuum adapter, according to claim 14.

The case of the inventive device is divided into two parts, of which the first part projects into the vacuum chamber or defines with at least one surface the vacuum of the vacuum chamber; and the second part of the case is located outside the vacuum chamber.

The vacuum chambers are not the process vacuum chambers, but, for example, transfer or lock chambers of the production system. Special measurement chambers, to which the inventive device can also be attached, can also be integrated into the production system. The samples to be measured are brought to the device for measurement purposes by means of the transport means, such as robots, which are present in the production system in any event. Then said samples are positioned in the immediate vicinity of the first part of the case.

The inventive device exhibits at least one adjusting device, which engages with the case and whose purpose is to change the position relative to the vacuum chamber or relative to the sample to be measured. Thus, it is guaranteed that the device can be adjusted prior to each measurement, a condition that can be necessary for many a measuring method. It is necessary especially when the demands on the measuring accuracy are high or when the positioning of the sample by the transport means in the process system is too inaccurate.

It is possible to adjust the device prior to every measurement without interrupting the production process by means of the means to dispose sealingly and moveably the case in the wall of the vacuum chamber. In addition, with these means the device can be uncoupled mechanically from the vacuum chamber. Furthermore, the device can be assembled and tested independently of the vacuum chamber.

The inventive device exhibits a counterpull device, which engages with the second part of the case and permits a force to act that acts against the force, acting on the device owing to the negative pressure of the vacuum of the vacuum chamber. Thus, the goal of a force-free and tension-free state of the device is achieved, a state that leads to a better operating mode of the individual components and a higher reliability and measuring accuracy. In particular, it makes it easier to adjust the device. Even the mechanical uncoupling of the device from the vacuum chamber is thus increased. A special advantage lies in the fact that the arrangement eliminates the need to use especially heavy duty motors for the adjusting device. Consequently small motors and correspondingly weak spindle drives, which have to be designed only to compensate for any reset forces of the means to dispose the case in a sealed and moveable manner in the wall of the vacuum chamber, are sufficient.

It has proved advantageous to install, among other things, bellows as the means for the sealing and moveable arrangement of the case in the wall of the vacuum chamber. Since the bellows do not exhibit any rigid expansion, they permit the position of the device to be adjusted in relation to the vacuum chamber or to the sample to be measured without having to accept any losses in the sealing effect. In addition, said bellows damp possible oscillations of the vacuum chamber relative to the device. In the event of lower vacuum and minimum adjustment paths, elastic seals are also conceivable.

To apply the counterforce, a spring suspension or a magnetic suspension is, for example, also conceivable. Preferred is a negative pressure chamber that is formed on the side of the device opposite the vacuum chamber and which is evacuated either separately or is connected to the large vacuum chamber of the production system by way of a vacuum connection so that the pressure is automatically compensated. In this second case the negative pressure chamber has a variable volume. Advantageously the measurement system is housed in the second part of the case.

In the measurement system there is an input signal, which is converted into a measurement signal through interaction with the sample. The input signal can be arbitrary electromagnetic waves. The input signal can be generated either directly in the measurement system or fed from outside the measurement system into the measurement system and can be, for example, monochromated or modulated there or modified differently to match the measurement conditions.

In addition, the measurement system includes at least one detector, which serves to detect the measurement signal. The evaluation of the measurement signal can take place in the measurement system. However, for the purpose of evaluation, the detection signal can also be sampled from the measurement system or stored inside or outside the measurement system.

The first part of the case serves to form the boundary between the vacuum in the production system and the atmosphere, i.e. usually air, in the measurement system in the second part of the case. The interface can be designed, for example, as a window, which is appropriate for a vacuum or a high vacuum and which is transparent for the input signal and the measurement signal.

Preferably the measurement system of the device, according to the invention, is designed in such a manner that it exhibits not only the at least one detector but also at least one light source or light feed, such as a fiber optic cable. Thus, optical measurements in the vacuum can be carried out with the device, according to the invention. The embodiment of the inventive device is appropriate especially for measurements on the surface of a sample, such as ellipsometric measurements to determine the thickness and the refractive index of coatings or also to determine the existing particles by measuring the scattered light or measuring the loss of the direct reflection on the sample or in a volume. These applications are appropriate especially—but not only—for the quality control in production processes in the semiconductor industry.

To carry out optical measurements in the vacuum, the first part of the case is designed as a vacuum adapter and exhibits a beam tube, through which the incoming beam is guided as the input signal, which was generated by the light source in the measurement system, and through which the emerging beam of the measurement signal is guided. The incoming beam does not have to be automatically generated by a light source inside the measurement system, but rather can also be generated outside the measurement system and be fed to the measurement system, for example, by way of light guide cables and emerge there as a light beam. The beam tube of the vacuum adapter is fastened with one end to that part of the case that contains the measurement system. By means of the vacuum adapter, it is possible to couple in, for example, an ellipsometer, a reflectometer and/or an FTIR [=Fourier transform infrared] spectrometer.

To ensure the desired measurement configuration or measurement geometry at the measurement site, the vacuum adapter exhibits advantageously a prism and/or a lens system on the end of the beam tube that faces the vacuum chamber. Beam properties, like divergence, dispersion and angle in relation to the sample, can be adapted to the specific features directly before the measurement and directly after the measurement. In lower vacuum it is possible to seal the prism or the lens system so as to be vacuum tight with the beam tube so that these optical elements act as interfaces between the atmosphere in the beam tube or the measurement system and the vacuum outside the device.

If the goal is supposed to be a very high measurement accuracy, the preferred solution is that such optical elements as the prisms or the lenses be located completely in the vacuum, since otherwise stress could be generated inside this optical system. The end of the beam tube that faces the measurement system exhibits advantageously a window, which is appropriate for a vacuum and is transparent to light of any wavelength. This vacuum window separates the atmosphere in the measurement system from the vacuum of the beam tube or the vacuum chamber. A vacuum prevails inside the beam tube.

Especially for ellipsometric applications of the device, it is advantageous to dispose the polarizer not necessarily in the measurement system, but rather to attach the polarizer on the beam tube interior or beam tube exterior of the prism system of the vacuum adapter. If a very high degree of polarization is relevant, the polarizer is attached preferably on the beam tube exterior of the prism system. Of course, for applications in high vacuum it can happen that, if it involves a polarization foil or the polarizer is attached by cementing on the prism system, the vacuum is affected negatively. In this case the polarizer is attached preferably to the beam tube interior.

Depending on the geometric features of the vacuum chamber, it can be necessary to design the beam tube of the vacuum adapter with a minimum cross section or curved. For these cases the beam tube of the vacuum adapter has advantageously deflecting prisms to guide the beam.

For the quality of the measurement results an accurate finding of the position of the sample in relation to the measurement beam is advantageous. To this end, the measurement system, disposed in the device of the invention, exhibits not only a measuring unit, which can be, for example, an ellipsometer, a reflectometer or a FTIR spectrometer but also an adjusting unit. The adjusting unit comprises at least one light source and at least one position sensitive detector. Preferably an adjusting laser is installed as the light source. Due to the installation of, for example, beam splitters, a light source, which may or may not also be present in the measuring unit, can be used simultaneously for the adjusting unit. The beam plane of the adjusting unit is moved parallel to the measurement geometry so that the system's state of adjustment can be reproduced as correctly as possible.

In an especially preferred embodiment a triangulation configuration is used as the adjusting unit. Thus, both the sample spacing and the tilt can be measured automatically. In this case the adjusting unit comprises an adjusting laser, a beam splitter and two position sensitive detectors. The laser beam from the adjusting laser is split by means of the beam splitter into two beams that are moved so as to be parallel. The one beam is used to determine the sample spacing. When the spacing between the samples changes, the point of impingement on the sample surface and thus also the reflected beam's point of impingement on one of the position sensitive detectors moves. The deviation from the desired value can be determined electronically and, if desired, can be used for an automatic correction by means of the servomotors. To determine the sample tilt, the second partial beam is used. When the sample tilts, this beam migrates to the second position sensitive detector, a state that can be determined in turn electronically. The tilt of the sample can be corrected mechanically, or the angle of tilt can be determined quantitatively and then taken into consideration during the evaluation of the measurement.

For tests, in which not only one point but also several points on the sample have to be measured, it has proved advantageous to use rotating sample tables. Between two measurements the sample can be further rotated about a specific angle by means of the rotating table. Preferably the rotating table is disposed on a linear table.

The linear table's direction of movement is in the radial direction of the rotating table. Through a combination of translational and rotational motions, an even greater number of measurement points can be approached on the sample surface. Especially compact is a variant, where not the rotating table is disposed on a linear table, but deflecting prisms or mirrors are spaced at a specific distance from the rotating table so that they can be moved linearly in the radial direction of the rotating table. Through a combination of linear movements of the about the prisms or mirrors and the rotating movements of the rotating table, just as many measurement points can be approached as in the embodiment described above. [sic]

The device, according to the invention, exhibits many advantages. Since the inventive device permits the integration of the measurement process into the production process in that it is carried out between the process steps and there is no need for the sake of adjustment to intervene in the operating mode of the production system, the goal is reached, on the one hand, that the samples can be measured extremely process oriented and, on the other hand, that the measurements can be carried out in such a manner that production and measurement do not exert a mutual negative effect. At this stage it is now possible to measure arbitrary samples without disturbing the production process and to achieve thereby maximum measurement accuracy. Eliminated are the cost intensive intermediate paths between the individual process steps and the measurement and, above all, the long reaction time between the detection of production errors and the reaction thereto.

Since the measurement configuration or the measurement geometry can be uncoupled from the design of the measurement system by means of the vacuum adapter, the measurement system can be optimized for higher measurement accuracy in an economical design. In addition, the entire device can be easily adapted to the space conditions in already existing production systems. To retrofit already existing production plants, it suffices to introduce the vacuum adapter into the vacuum through an opening in the respective vacuum chamber.

Since the measurement system is not located under vacuum, maintenance work and retrofitting work can be done on the measurement system without having to ventilate the process line or the respective vacuum chamber. Even the expense of building the measurement system decreases, since it is not necessary to use vacuum appropriate components, such as cable ducts. In addition, the negative effect on the volume in the sample or measurement surroundings, for example, due to the electrical components is prevented.

Several devices of the invention can be integrated in such a manner at diverse points of the production process that they are adapted to the production process of the respective product. Since the retrofitting of the production systems with the inventive device is associated with little cost and the inventive device itself is economical due to its simple construction, there is the possibility of setting up a comprehensive quality control system inside the production process at a low investment cost.

BRIEF DESCRIPTION OF THE SEVERAL VIEWS OF THE DRAWINGS

The invention shall be explained in detail with reference to the example of an ellipsometric measurement of wafer surfaces.

Figure 1C:
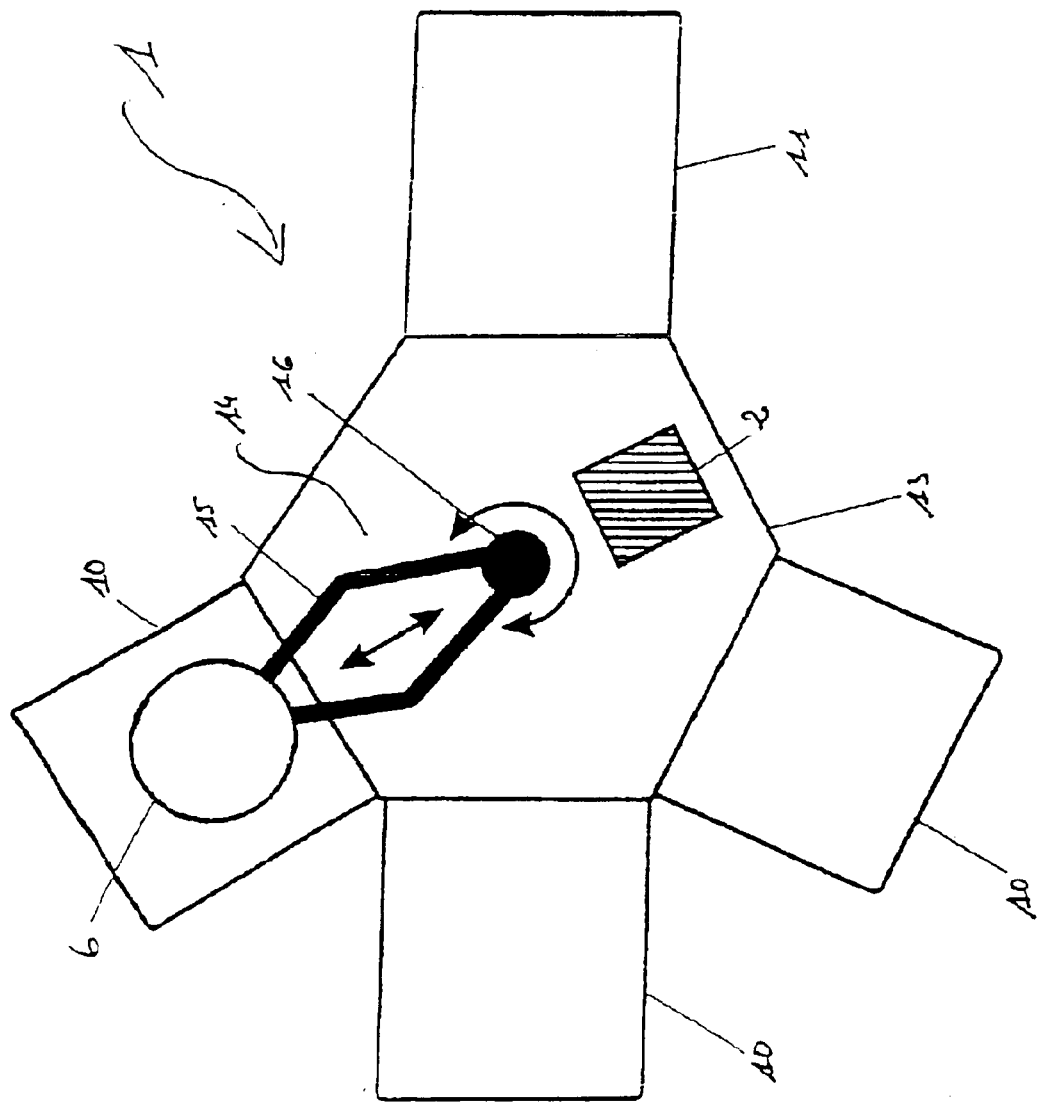
Figure 2A:
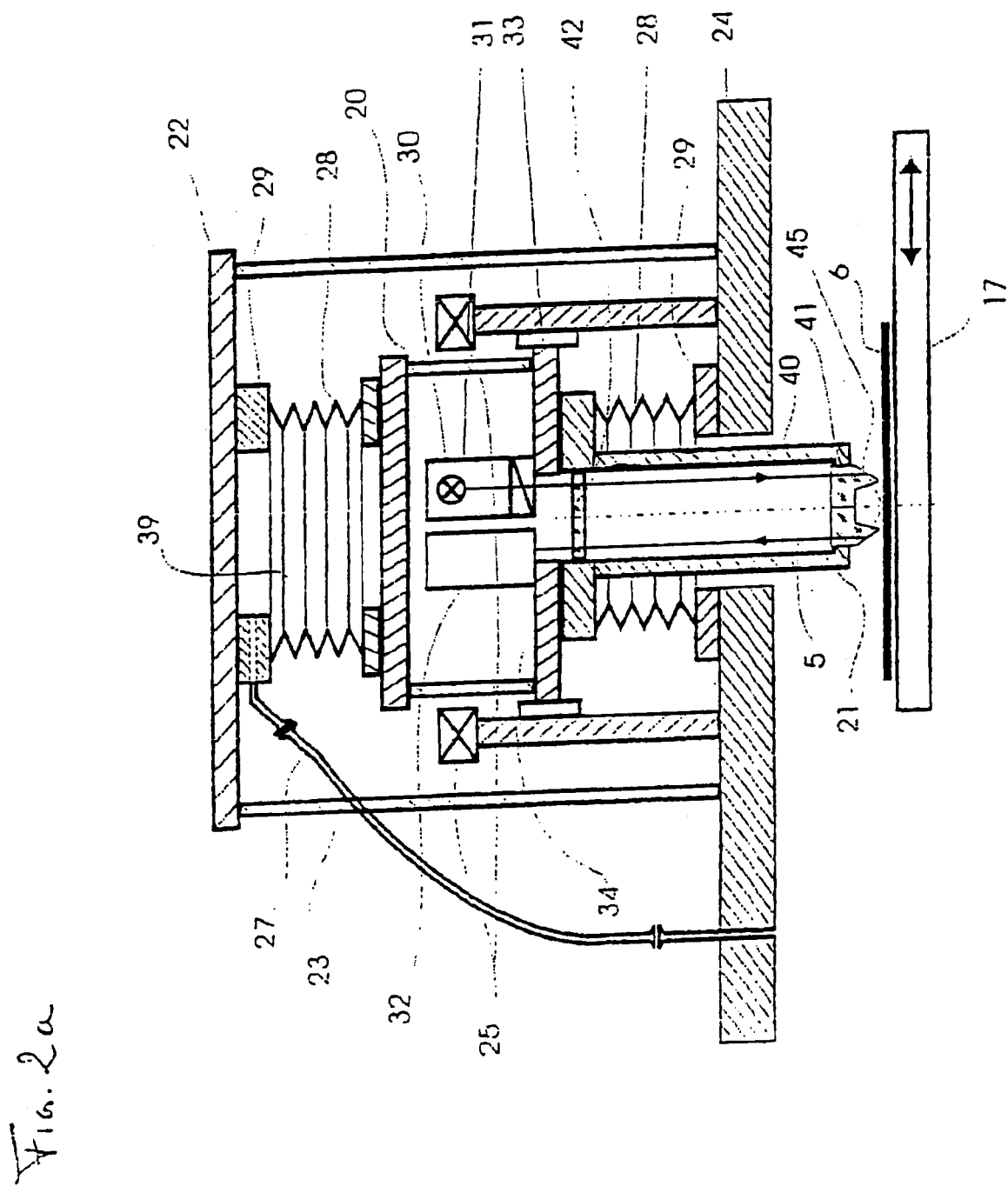
Figure 2B:
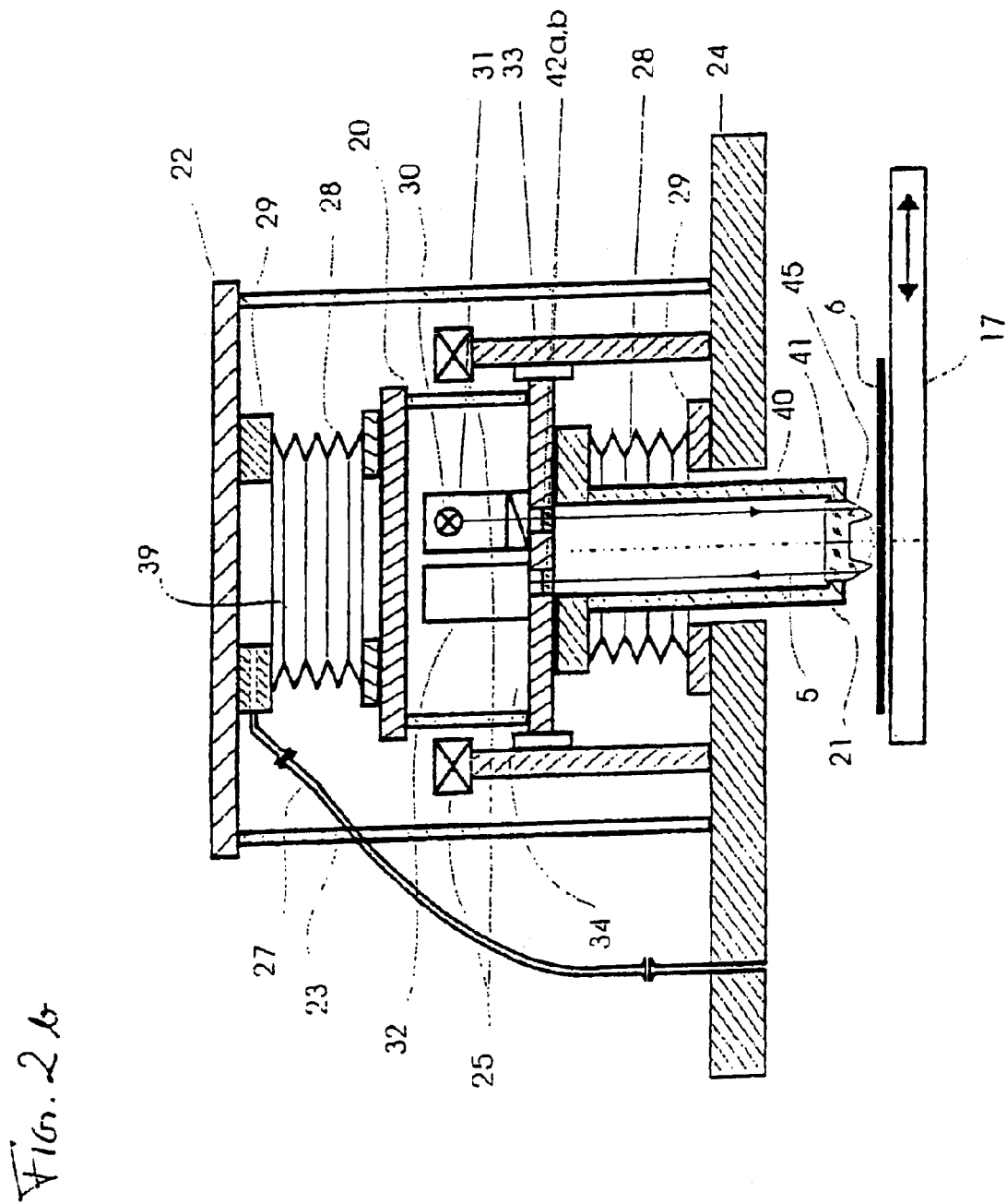
Figure 3A:
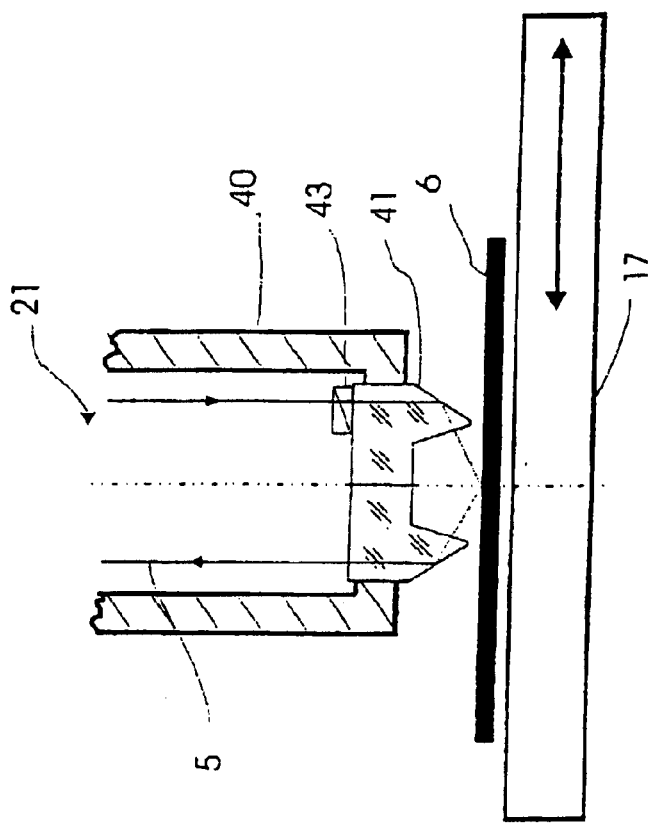
Figure 3C:
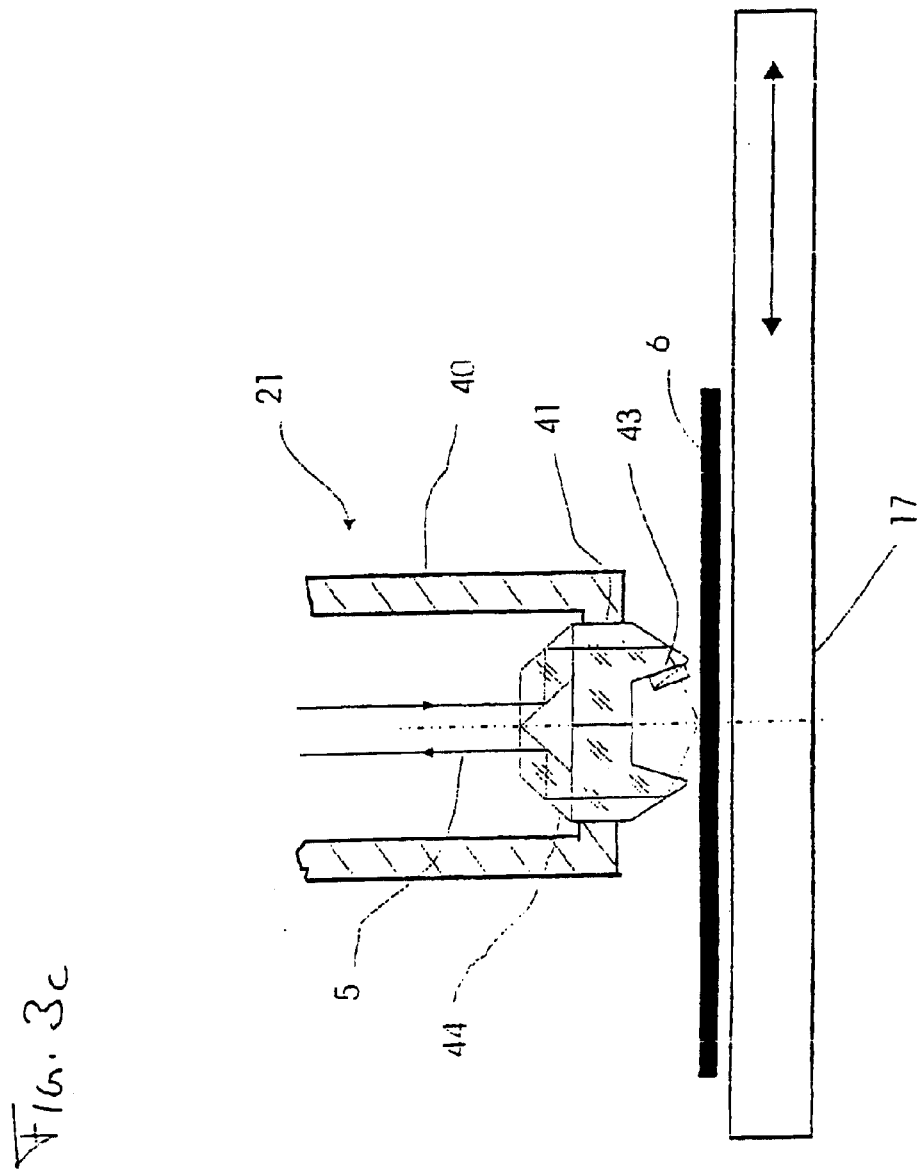
Figure 4A:
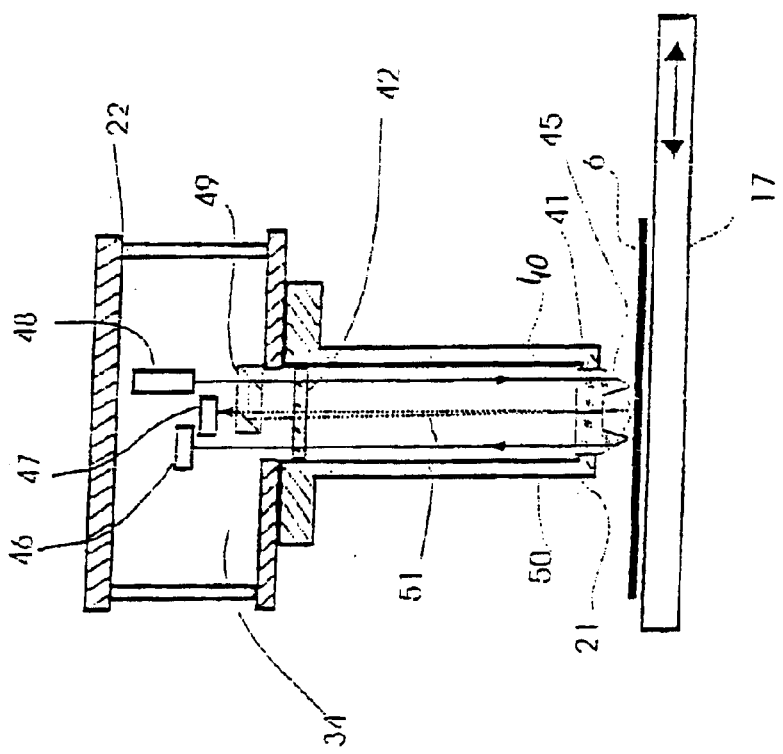
Figure 4B:
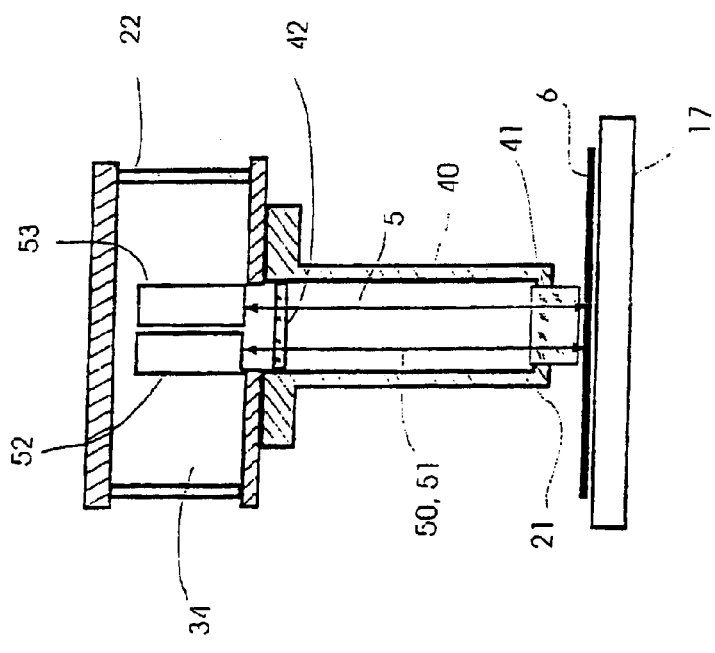
Figure 5A:
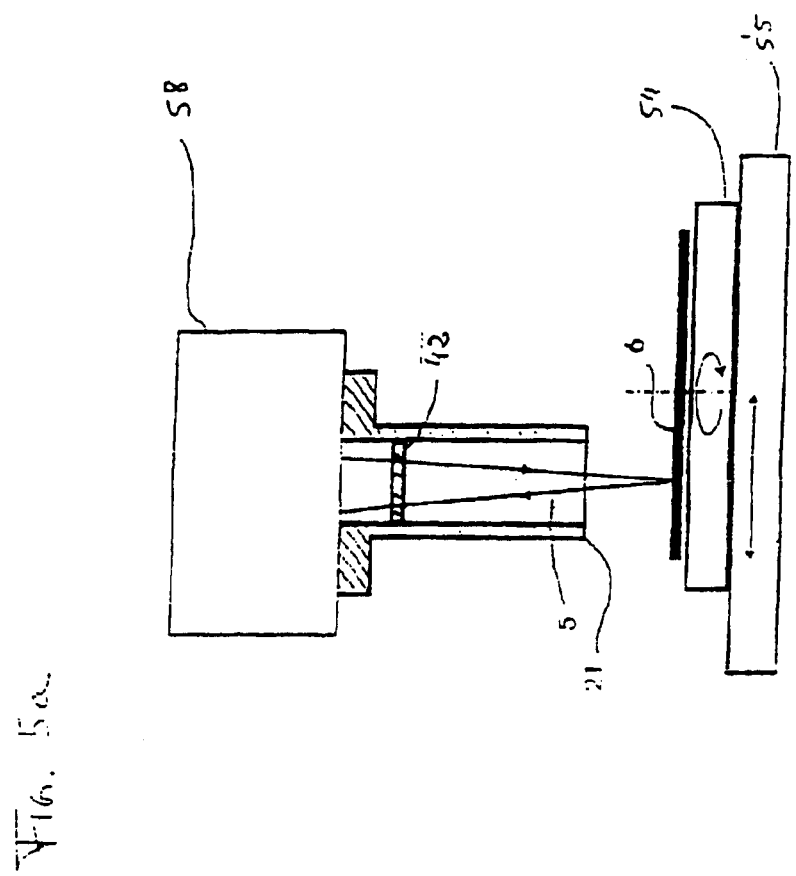
Figure 5B:
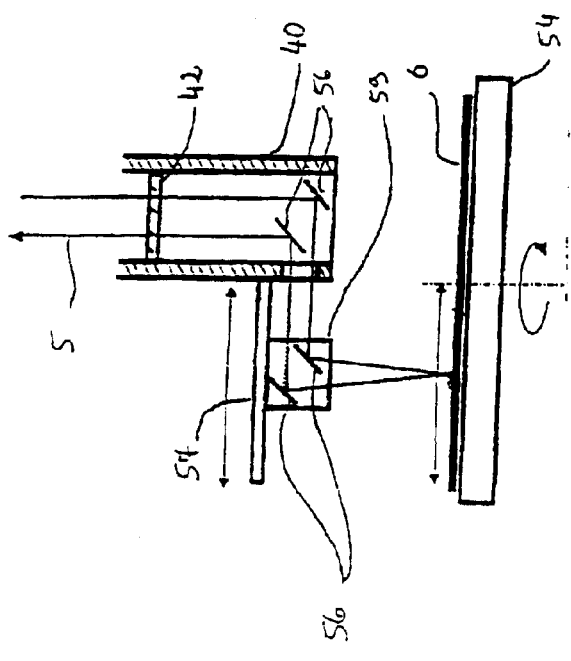

| | |
|---|---|
| FIGS. 1a, 1b and 1c | depict possible positions in the device inside a wafer production system. |
| FIGS. 2a and 2b | depict two possible embodiments of the device, according to the invention. |
| FIGS. 3a, 3b and 3c | depict three possible embodiments of the vacuum adapter, according to the invention. |
| FIGS. 4a and 4b | depict a device with adjusting unit; and |
| FIGS. 5a and 5b | depict devices with rotating sample table. |

DETAILED DESCRIPTION OF THE INVENTION

FIG. 1a depicts a wafer production system 1. It has a modular design comprising process chambers 10, a lock chamber 11 and a transfer chamber 13. Such wafer production systems are called cluster systems.

The wafers 6 are fed through the lock chamber 11 into the vacuum of the cluster system 1. By means of a robot 14, which comprises in essence a robot arm 15, which rotates around the robot axis 16, and is disposed in the transfer chamber 13, the wafers 6 are transported out of the lock chamber 11 into the various process chambers 10.

In FIG. 1a the cluster system 1 exhibits, besides the two process chambers 10, also a measurement chamber 12. The device 2, according to the invention, is attached to this measurement chamber 12. There the wafer 6 is measured, before it is coated in a process chamber 10. After the coating step, the measurement is repeated; and the layer thickness and the refractive index of the layer are determined by means of the measurements, carried out by means of the device chamber. With these data it can be determined whether the coating process was done correctly. After the measurement the wafer 6 is transported by the robot 14 into the next process chamber 10, and the production process is continued. Optionally even after the measurement in the second coating step the wafer can be measured again in the measurement chamber 12.

FIGS. 1b and 1c depict two other cluster systems 1. These two cluster systems 1 exhibit three process chambers 10. Thus, no separate chamber is provided for the measurement of the wafers 6. In FIG. 1b the device of the invention is attached to the lock chamber 11. The wafers 6 are measured upon entry into the cluster system 1; and after passage of the three process steps, which take place in the three process chambers 10, they are measured again.

FIG. 1c shows the third possibility for positioning the device 2. Here the device 2 is attached in the transfer chamber 13. There the wafers 6 can be measured, as desired, before or after each process step.

FIG. 2a shows a preferred embodiment of the device, according to the invention. The core members of the device, according to the invention, are the first part of the case 21, designed as a vacuum adapter, and the measurement system 34 in the second part of the case 20.

The measurement system 34 comprises a light source 30, a polarizing unit 31, and an analyzing unit 32. The light source 30 is a photodiode, which generates a laser beam with a wavelength of 635 nm. They form together an ellipsometer, which is disposed on the ellipsometer base plate 33. The second part of the case 20 is arranged around the ellipsometer.

The vacuum adapter 21 is flanged to the part of the case 20, more explicitly to the ellipsometer base plate 33. The vacuum adapter 21 exhibits a beam tube 40, in which the light beam, generated by the light source 30, and the measuring beam 5 travel. A vacuum window 42 forms the transition between measurement system 34 or the second part of the case 20 and the vacuum adapter 21. Said window is transparent to the light beams, but seals effectively the vacuum in the first part of the case 21. Each part of the case 20, 21 includes chambers, which are separated from each other, whereby the separation is guaranteed by the vacuum window 42.

A measurement window 45, designed as a prism system 41, is arranged on the other end of the beam tube 40. It is not connected vacuum-tight to the beam tube 40 so that inside the beam tube 40 the same vacuum prevails as in the vacuum chamber. The prism system 41 is designed in such a manner that the result is an angle of incidence ranging from 65 degrees to 75 degrees, which is optimal for ellipsometric measurements.

That part of the case 20, which contains the measurement system 34, and the vacuum adapter 21 are attached to the cover plate 24 of the vacuum chamber by means of bellows 28 and a flange 29. In so doing, the flange 28 envelops the vacuum adapter 40 and stands perpendicularly on the wall 24 of the vacuum chamber. Owing to the bellows 28 the ellipsometer base plate 33 and the cover plate 24 of the vacuum chamber are uncoupled mechanically from each other. Oscillations of the cover plate 24 of the vacuum chamber are not transferred to the ellipsometer base plate 33. Therefore, the measurement is not falsified by any oscillations.

To measure the surface of a wafer 6, the wafer 6 is slid under the prism system 41 of the vacuum adapter 21 of the device by means of a sample feed 17, which is attached to a robot. The sample feed 17 is designed in such a manner that the surface of the wafer 6 can be scanned over the entire surface.

Prior to the measurement the embodiment of the inventive device, depicted in FIG. 2, is installed on a level with the device in relation to the wafer surface. To this end, both sides of the measurement system 34 exhibit a motor 25 with a spindle drive. In an embodiment of the device that is not illustrated, the measurement system 20 exhibits another light source and another detector, with which the position of the wafer surface is measured in relation to the measurement system 20. In the case, depicted in FIG. 2a, the desired position is determined in that the measurement beam 5 impinges on a specific point of the detecting surface of the detector 32; and at that point there is an intensity maximum.

To design a force-free variable height adjustment, other bellows 28, which are connected to a cover plate 22 by means of a flange 29, are arranged over the part of the case 20 (of the measurement system 34). The cover plate 22 rests on supports 23. Together with the cover plate of the part of the case 20, the cover plate 22 and the bellows 28 form a negative pressure chamber 39 with variable volume.

The negative pressure chamber 39 is connected to the vacuum chamber in the cluster system by means of the vacuum attachments 27 and a vacuum connection 26. Thus, the same vacuum prevails in the negative pressure chamber 39 as in the vacuum chamber. The negative pressure in the chamber 39 with variable volume counteracts the negative pressure, which acts, starting from the vacuum chamber, on the vacuum adapter 21 and that part of the case 20 that contains the measurement system 34. Therefore, the motors 25 have to generate less force to adjust the height of the measurement system 34 and the vacuum adapter 21. During the adjustment process, the volume of the negative pressure chamber 39 changes and thus a pressure compensation takes place automatically over the vacuum connection 26. Thus, it is guaranteed that the device is always in a state of minimum or negligeably small forces.

The motors 25 and also the measurement system 34 are not located in the vacuum. Thus, very conventional components can be used that do not have to be vacuum appropriate. Furthermore, they cannot exert a negative effect on the vacuum in the sample or measurement surrounding. If the measurement system 34 or the motors 25 have to be changed or adjusted in any way, it can be done without having to ventilate the vacuum chamber. Therefore, the production process can continue undisturbed.

FIG. 2b depicts a modification of the embodiment of FIG. 2a. Instead of only one vacuum window 42, the vacuum adapter 21 exhibits two vacuum windows 42a and b. The incident beam from the measurement system 34 enters through the vacuum window 42a into the vacuum adapter 23; through the vacuum window 42b the measurement beam 5 from the vacuum adapter enters into the measurement system 34. Since the window areas are smaller, the forces, generated by means of negative pressure, are smaller on the window; and consequently lower mechanical stresses are generated in the glass that could falsify the measurement results.

FIG. 3a depicts that end of the inventive vacuum adapter 21 that projects into the vacuum chamber. A prism system 41, which deflects the beam at an angle of incidence of about 70 degrees, is introduced at the end of the beam tube 40. Following reflection on the surface of the wafer 6, the measurement beam 5 is guided perpendicularly to the top through the prism system 41.

The input polarizer 43, which is required for the ellipsometer, can be attached to different points of the system. In FIG. 2a it is located in the polarizing unit 31. In contrast, in FIG. 3a it is attached on the beam tube interior. Thus, the beam is polarized immediately before passage through the prism system 41. Thus, it is prevented that in passing through the vacuum window the polarization of the beam is modified too much. When the beam passes through the prism system 41, the polarization of the beam can also be changed somewhat, especially if stress is generated in the prism system.

Therefore, in FIG. 3b the polarizer is attached on the beam tube exterior of the prism system 41 and polarizes the beam immediately before impinging on the surface of the wafer 6. Of course, problems can occur, above all, in the high vacuum, if the polarizer 43 is a polarization foil or the polarizer 43 was cemented on. Because in this case gas evolution can take place that has a negative effect on the vacuum. Particles can also be produced that settle out on the wafer surface and thus make the wafer useless. Hence, where the polarizer is supposed to be arranged must be decided as a function of the application.

In the vacuum adapter, depicted in FIG. 3c, another prism system 44, which serves to exhibit the narrow beam guide inside the beam tube 40 of the vacuum adapter 21 in such a manner that an ideal measurement geometry is achieved on the sample surface, is disposed in front of the prism system 41. Deflecting prisms 44 can also be installed when the beams have to be guided around a corner inside the beam tube 40.

For the quality of the measurement results, it is necessary to find the precise sample position in relation to the beam, and in particular in relation to the sample spacing and the sample tilt. To determine automatically the sample spacing and tilt, a triangulation arrangement, as described in FIG. 4a, is proposed. The beam plane of the adjusting unit 53 is moved parallel with respect to the beam plane of the measuring unit 52 (FIG. 4b, side view of the arrangement from FIG. 4a) so that both beams pass through the prism in the same manner. Thus, it is guaranteed that the position sensor beams 50, 51 always give an accurate reproduction of the system's state of adjustment. In the case of an ellipsometric arrangement the measuring unit comprises the light source 30, the polarizing unit 31 and the analyzing unit 32 in FIG. 2b. However, the measuring unit can also comprise a reflectometer or an FTIR spectrometer.

The adjusting unit comprises the adjusting laser 48, the beam splitter 49 and the two position sensitive detectors 46 and 47. The beam from the adjusting laser 48 is split into two beams, which are moved so as to be parallel, by means of the beam splitter 49. A beam 50 traverses the prism block 45 and, thereby, touches the sample at the same angle as the measurement beam and then impinges on a position sensitive detector 46. When the spacing between the samples and the prism changes, the point of impingement on the sample surface moves laterally and thus also the point of impingement of the beam on the position sensitive detector 46. Thus, the deviation from the desired value can be determined electronically and, if desired, used for an automatic correction by means of three servomotors 25.

To determine the tilt, the second partial beam 51 is used. It is guided virtually perpendicularly through the prism 45 onto the sample surface and from there focused at the second position sensitive detector 47. When the sample is tilted, the beam migrates on the position sensitive detector 47, a feature that in turn can be determined electronically. A mechanical correction of the determined tilt is very time consuming. It is simpler to detect quantitatively the angle of tilt from the known geometry of the arrangement and then to consider arithmetically when evaluating the ellipsometric measurement.

FIG. 5a depicts a detail of another preferred embodiment of the inventive device. An infrared spectrometer 58 is installed as the measuring unit. Attached to it is a vacuum adapter 1, which is provided with a vacuum window 42, which is transparent to infrared radiation. The measurement beam 5 is guided in such a manner into the vacuum adapter that it impinges on the surface of the sample 6 at a very small angle of incidence. The sample 6 is deposited on a sample table, which is designed as a rotating table 54. The rotating table 54 in turn is arranged on a linear table 55. The direction of movement of the linear table 55 is radial to the axis of rotation of the rotating table 54. The rotating table 54 and the linear table 55 are dimensioned in such a manner that through a combination of rotational and translational motions of the two tables 54, 55 any arbitrary point on the surface of the sample 6 can be positioned in such a manner under the vacuum adapter 21 that the measurement beam can strike it.

The detail of an inventive device, depicted in FIG. 5b, also depicts a rotating table 54 as the sample table for the sample 6. Of course, in this case the rotating table 54 is not arranged on a linear table 55. Deflecting mirrors 56 to guide the beam are provided both inside and outside the beam tube 40. The deflecting mirrors 56, located outside the beam tube 40, are attached on a deflecting block 59, which is connected in turn to a linear motor 57. The direction of movement of the linear motor 57 is radial to the axis of rotation of the rotating table 54. Using the linear motor 57, the deflecting block 59 and thus also the deflecting mirrors 56 are moved radially to the sample surface. This in turn also changes the point of impingement of the measurement beam 5 on the surface of the sample 6. Through the combination of rotational motion of the sample and translational motions of the measurement beam the goal is reached that each point on the surface of the sample 6 can be measured.

List of Reference Numerals

| | |
|---|---|
| 1 | cluster system |
| 2 | device |
| 5 | measurement beam |
| 6 | wafer |
| 10 | process chamber |
| 11 | lock chamber |
| 12 | measurement chamber |
| 13 | transfer chamber |
| 14 | robot |
| 15 | robot arm |
| 16 | robot axis |
| 17 | sample feed |
| 20 | second part of the case |
| 21 | vacuum adapter |
| 22 | cover plate of the device |
| 23 | support |
| 24 | cover plate in the vacuum chamber |
| 25 | stepping motor with spindle drive |
| 26 | vacuum connection |
| 27 | vacuum attachment |
| 28 | bellows |
| 29 | flange |
| 30 | light source |
| 31 | polarizing unit |
| 32 | analyzing unit |
| 33 | ellipsometer base plate |
| 34 | measurement system |
| 39 | negative pressure chamber |
| 40 | beam tube |
| 41 | prism system |
| 42 | vacuum window |
| 43 | polarizer |
| 44 | deflecting prism |

-continued

List of Reference Numerals

| | |
|---|---|
| 45 | measurement window |
| 46 | position sensitive detector for determining the sample height |
| 47 | position sensitive detector for determining the sample tilt |
| 48 | adjusting laser |
| 49 | beam splitter |
| 50 | adjusting beam for determining the sample height |
| 51 | adjusting beam for determining the sample tilt |
| 52 | adjusting unit |
| 53 | measuring unit |
| 54 | rotating table |
| 55 | linear table |
| 56 | deflecting mirror |
| 57 | linear motor |
| 58 | infrared spectrometer |
| 59 | deflecting block |

What is claimed is:

1. A device to carry out measurements in a vacuum chamber, in particular to measure thin layers, with a case, exhibiting at least one measurement window, to receive a measurement system, comprising:
a two part case with a first part of the case, which projects into the vacuum chamber, and a second part of the case, which is located outside the vacuum chamber,
means for the sealing and moveable arrangement of the case in the wall of the vacuum chamber,
an adjusting unit, engaging with the case, and
a counterpull device, engaging with the second part of the case.

2. A device, as claimed in claim 1, wherein the means for the sealing and moveable arrangement of the case comprise bellows, resting against the outside of the wall of the vacuum chamber.

3. A device, as claimed in claim 1, wherein the counterpull device is a negative pressure chamber, adjacent to the second part of the case.

4. A device, as claimed in claim 3, wherein the negative pressure chamber is connected from the viewpoint of pressure to the vacuum chamber.

5. A device, as claimed in claim 3, wherein the performance of the adjusting unit is designed according to the weight of the case and the measurement system.

6. A device, as claimed in claim 1, wherein the measurement system is disposed in the second part of the case, which is separated from the viewpoint of pressure from the first part of the case.

7. A device, as claimed in claim 1, wherein the first part of the case is a vacuum adapter.

8. A device, as claimed in claim 1, wherein the measurement system comprises at least one light source or light feed and at least one detector.

9. A device, as claimed in claim 8, wherein the first part of the case is designed as a vacuum adapter and exhibits a common beam tube for at least one incoming and at least one outgoing beam.

10. A device, as claimed in claim 9, wherein the measurement window comprises a prism and/or a lens system.

11. A device, as claimed in claim 9, wherein the vacuum adapter terminates with at least one vacuum window on the end of the beam tube facing the measurement system.

12. A device, as claimed in claim 11, wherein a polarizer is attached on the beam tube interior or beam tube exterior of the prism system of the vacuum adapter.

13. A device, as claimed in claim 9, wherein in the beam tube of the vacuum adapter deflecting prisms or mirrors are disposed inside the vacuum adapter.

14. A device, as claimed in claim 1, wherein the measurement system exhibits a measuring unit and an adjusting unit comprising at least one light source and at least one position sensitive detector.

15. A device, as claimed in claim 14, wherein the adjusting unit exhibits an adjusting laser, a beam splitter and two position sensitive detectors.

16. A device, as claimed in claim 1, wherein it exhibits a rotating table as the sample table.

17. A device, as claimed in claim 16, wherein the rotating table is arranged on a linear table, whose direction of motion runs radially to the rotating table.

18. A device, as claimed in claim 16, wherein the deflecting prisms or mirrors are spaced in such a manner relative to the rotating table that they can be moved linearly in the radial direction of the rotating table.

* * * * *